United States Patent [19]
Baron et al.

[11] Patent Number: 5,752,827
[45] Date of Patent: May 19, 1998

[54] PERIODONTAL EXAMINATION APPARATUS AND METHOD OF USE

[76] Inventors: Yuda Baron; Anne Baron, both of 825 Sutter Ave., Palo Alto, Calif. 94303

[21] Appl. No.: 707,639

[22] Filed: Sep. 5, 1996

Related U.S. Application Data

[63] Continuation-in-part of Ser. No. 325,961, Oct. 20, 1994, abandoned.

[51] Int. Cl.$^6$ .................................................. A61C 19/04
[52] U.S. Cl. .............................. 433/68; 433/72; 433/29; 128/776
[58] Field of Search ............... 364/705.06, 705.07, 364/705.08, 709.01, 709.03, 709.04, 708.1; 433/72, 75, 29, 215, 229, 68; 128/776

[56] References Cited

U.S. PATENT DOCUMENTS

| | | | |
|---|---|---|---|
| 3,943,914 | 3/1976 | Grenfell et al. | 433/72 X |
| 4,402,056 | 8/1983 | Sado et al. | 364/705.06 |
| 4,444,520 | 4/1984 | Hanakata et al. | 400/88 |
| 4,764,114 | 8/1988 | Jeffcoat et al. | 433/72 |
| 5,084,833 | 1/1992 | Matsuda et al. | 364/709.04 |
| 5,274,798 | 12/1993 | Aihara et al. | 395/575 |
| 5,305,181 | 4/1994 | Schultz | 364/708.1 X |
| 5,318,442 | 6/1994 | Jeffcoat et al. | 433/72 |
| 5,329,106 | 7/1994 | Hone et al. | 235/472 |

OTHER PUBLICATIONS

Dental Hygiene Theory and Practice, Darby and Walsh, text book pp. xv, 123,124,175,187,189,194 (1994).

Clincal Practice of the Dental Hygienist, Wilkins, text book pp. 58–61,176–179,186–195,746,747 (1976).

*Primary Examiner*—Nicholas D. Lucchesi
*Attorney, Agent, or Firm*—Ray K. Shahani

[57] ABSTRACT

A periodontal examination data recording and recall method and apparatus. The periodontal examination method includes obtaining an automated periodontal examination data recording and recall apparatus having at least one pre-programmed mode of operation whereby periodontal examination data is entered in a predetermined sequence, performing the periodontal examination and collecting the periodontal examination data, entering the periodontal examination data into the periodontal examination apparatus, the periodontal examination data obtained through the periodontal examination performed in a predetermined sequence, and storing the periodontal examination data for future use, including review and display. The periodontal examination apparatus includes a keypad input device, an LCD, a main controller, an attachment device for securing the apparatus to the examiner's arm or other portion of the armamentarium, and is provided with at least one automatic input sequence. The user can choose either an automatic sequence, or select random periodontal examination data input. The user can also choose to review previously entered periodontal examination data. Periodontal examination data can either be stored solely in the periodontal examination apparatus or it may be transmitted to an external device.

7 Claims, 15 Drawing Sheets

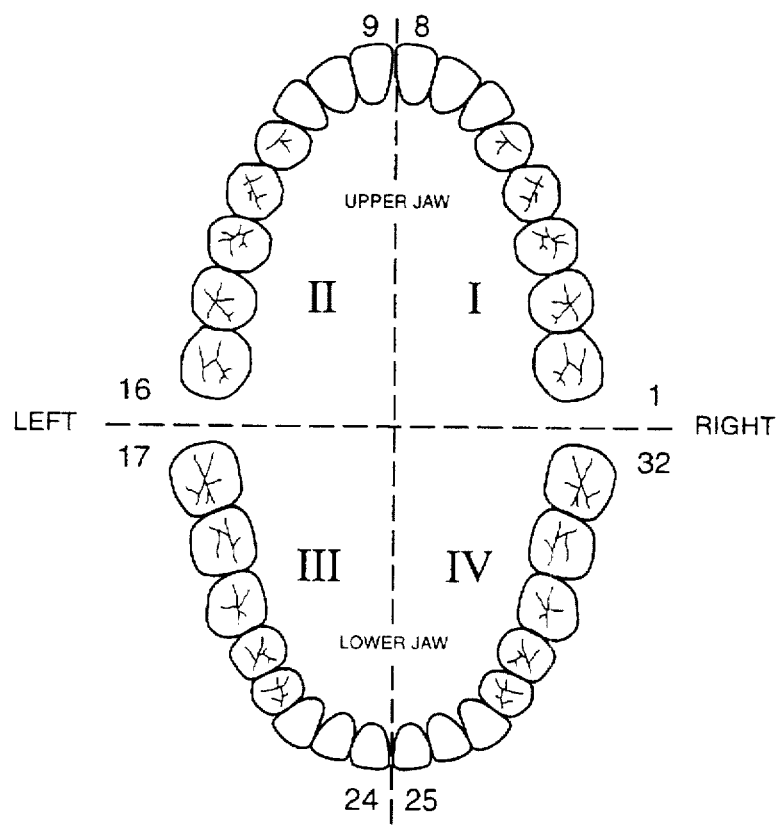
FIG. 1
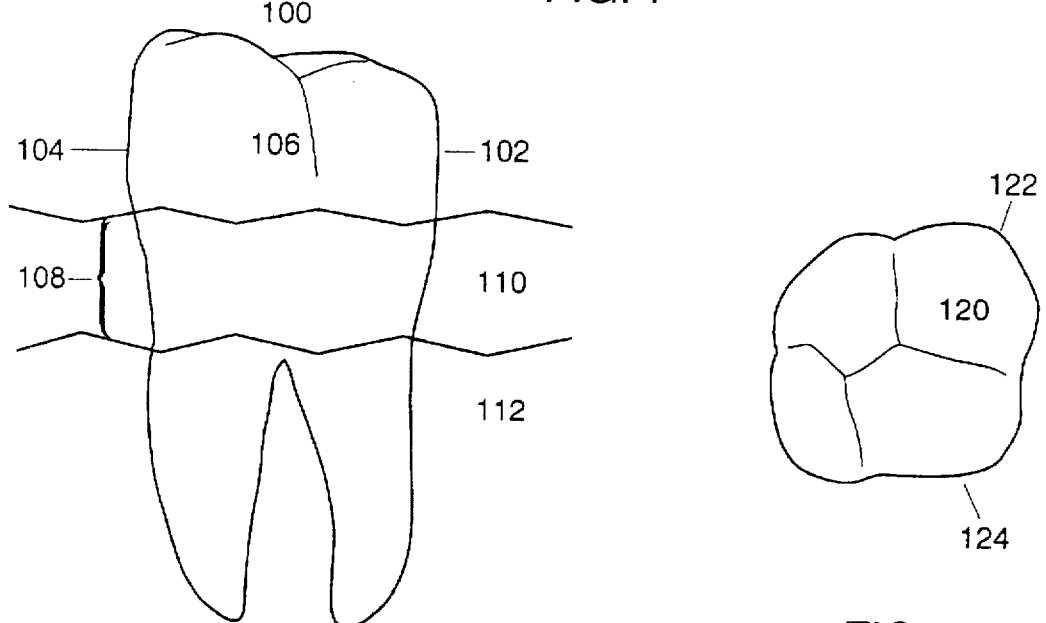
FIG. 2A
FIG. 2B

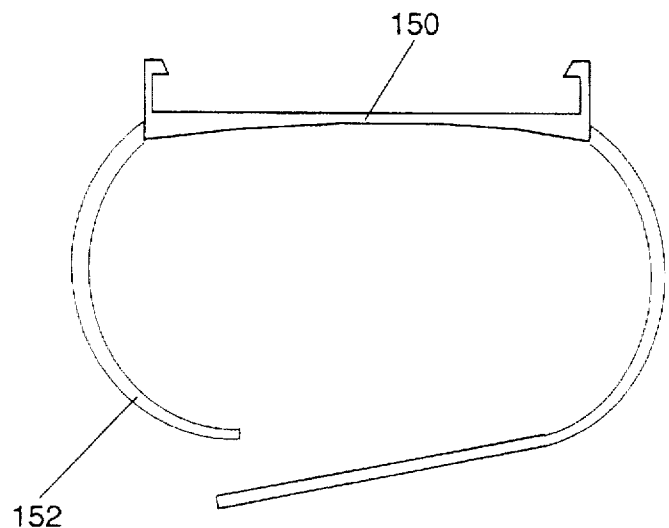
FIG. 6
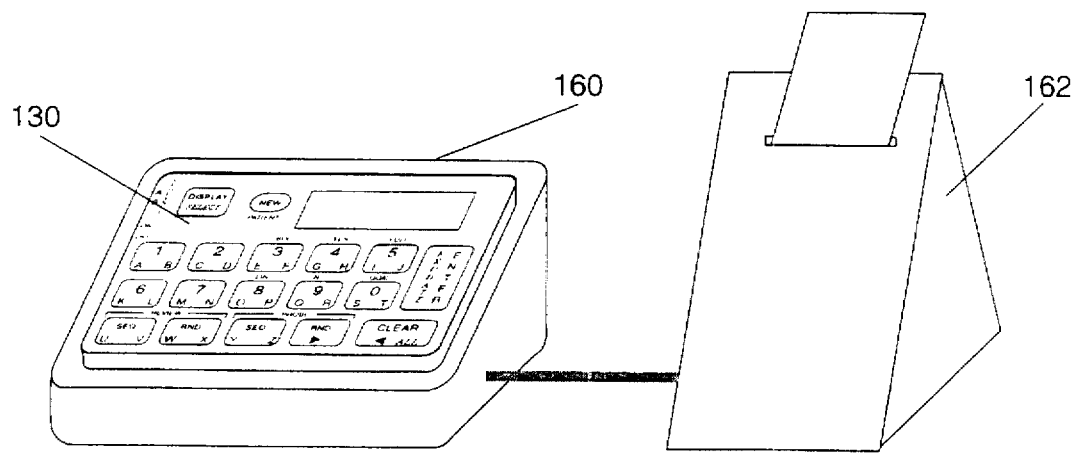
FIG. 7
| 1 | 2 | 3 | 4 | 5 | 6 | 7 | 8 | |
|---|---|---|---|---|---|---|---|---|
| 7 5 | 7E 4E | 8E 4 | 4E 3 | 5 6 | 3E 4E | 2 3 | 2 4 | — 190 |
| 7 | 3EF | 5F | 2E | 4 | 3 | 3E | 0 | |
| M | | M | M | M | | | | |
| 3E 2 | 7 4E | 8E 5 | 6E 2 | 5 6 | 3E 4E | 3 3 | 3 5 | |
| 1 | 4E | 6 | 4E | 5 | 3 | 5E | 1 | |
FIG. 11

PERIODONTAL EXAMINATION APPARATUS AND METHOD OF USE

This application is a continuation in part of Ser. No. 08/325,961, filed Oct. 20, 1994, now abandoned.

FIELD OF THE INVENTION

The present invention relates generally to methods and apparatus for performing periodontal procedures, and more specifically to a novel method for performing a periodontal examination utilizing an intelligent, prompting periodontal data recording and recall apparatus.

BACKGROUND OF THE INVENTION

A periodontal examination is an important procedure performed frequently in dental and periodontal offices. A periodontal examination is an examination of the bones which hold the teeth in place as well as the conditions of the teeth and gums in specific regions. The procedure includes probing the teeth and the gums around each of the patient's teeth in succession, and recordation of probing and other data relative to each tooth. Since the examination requires several measurements for each tooth, there being 32 teeth total normally, a large amount of periodontal data is generated:

If a single individual is performing the examination, it can be quite tedious in that the practitioner must examine the tooth, record the periodontal data on a paper chart, then return to the patient's mouth. Given the current concepts in infection control, promulgated in standards and regulations by OSHA, the EPA and other federal agencies, maintaining a safe and clean environment free of risk of contamination by infectious disease is of utmost concern to the modern dental practitioner.

If one person is performing the examination, he must first probe one tooth, then put down his instruments and put on an over-glove to write down examination data from only that first tooth on a paper chart. The examiner then removes the over-glove, at which point he is ready to continue to probe the next tooth.

Traditionally, in order to avoid this tedious and time consuming process, two people work together to perform the exam. The first does the actual examination, while the second person records the data. While the use of an assistant greatly speeds the examination process, this luxury is not always available. If an assistant is available, the dental practice must shoulder significant additional expense.

However, heretofore there were only two known alternatives to overcome the need for a second person to reduce the time required for a single individual to perform the examination. The first method to automatically store the examination data is a large voice-activated computer system. While this system works quite well, the cost is as high as $25,000 to $30,000 and is prohibitive to most practitioners. Equally as expensive or more so and also prone to error due to imprecise use, inconsistent patient oral structure an other reasons, another system includes a sensor probe which is placed at a specific measurement surface, the practitioner activates the sensor to take the specific measurement, and the sensor probe measures and transmits that data via display, electric wire or other transmission means.

SUMMARY

The periodontal examination apparatus includes a keypad, a liquid crystal display (LCD), microcontroller, and optionally an external device such as a printer, computer, etc. Data can be recorded and recorded data can be retrieved. In recording mode, the practitioner may select between entering periodontal data randomly or according to predetermined and automatic input sequences for probing the full mouth or for individual quadrants only. The user can also choose to review data stored in the apparatus or elsewhere, also either randomly or according to predetermined and automatic display sequences. Data may be stored in the periodontal examination apparatus itself, or may be transferred to an external device.

Accordingly, it is an advantage of the present invention to provide a method for administration of periodontal examination in which accurate data is obtained by one person and is readily available for further storage or recall for numerous purposes.

It is a further advantage of the present invention to provide an apparatus to automatically and selectively receive data obtained in the periodontal examination and store such data for subsequent use.

Yet another advantage of the present invention is to provide a method and apparatus for guiding a practitioner through an examination with an operating program which requests information via display in a sequential, prompted sequence and information is readily available throughout the procedure Another advantage of the present invention to provide an apparatus that is small and lightweight and can be worn on the arm, wrist, mounted on the dental chair, lamp, or other operative position within the practitioner's armamentarium.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 1 is a representative view of the numbering and quadrant identification nomenclature implemented in the method and apparatus of the present invention. The teeth on the upper jaw are distinguished from those of the lower jaw.

FIG. 2A is a representative side perspective view of a common tooth showing the different surfaces of the tooth to be examined in the preferred method of the present invention.

FIG. 2B is a representative top perspective view of a common tooth showing the different surfaces of the tooth to be examined in the preferred method of the present invention.

FIG. 6 is a representative cross section view taken at 6 of the method and apparatus of the present invention.

FIG. 7 is a representative view of the periodontal examination apparatus of the present invention installed in a desktop retainer.

FIG. 11 is a representative printed label showing periodontal examination data collected and generated using a preferred embodiment of the method and apparatus of the present invention.

DETAILED DESCRIPTION OF THE INVENTION

Figure 3:
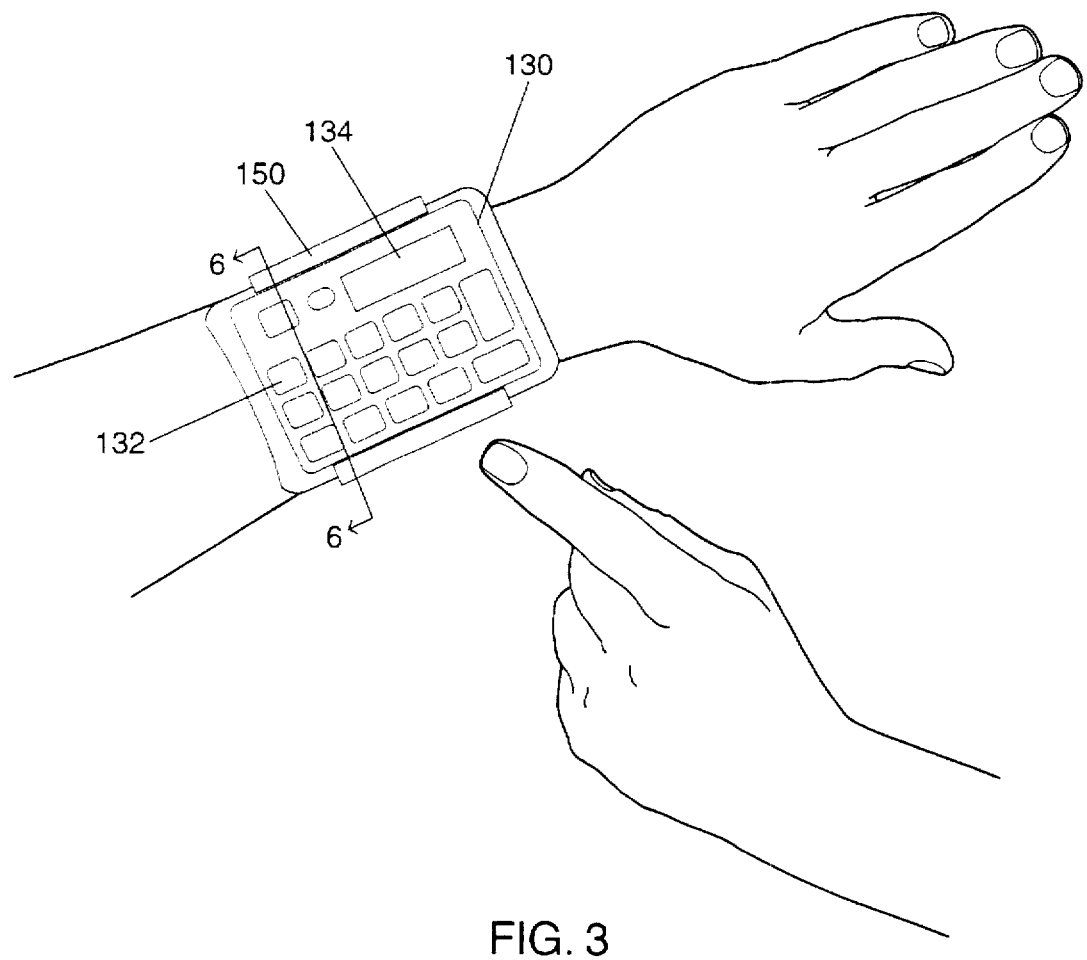
FIG. 3 is a representative perspective view of the method and apparatus of the present invention.

FIG. 1 is a representative view of the numbering and quadrant identification nomenclature implemented in the method and apparatus of the present invention. The teeth on the upper jaw are distinguished from those of the lower jaw. The four quadrants are indicated by Roman numerals I–IV. The numbering and position nomenclature as used herein will be understood by those skilled in the art.

FIG. 2A is a representative side perspective view of a common tooth showing the different surfaces of the tooth to be examined in the preferred method of the present invention. With regard to the tooth 100, it will be understood that the distal surfaces 102 are the surfaces nearer the back or rear portion of the mouth and the mesial surfaces 104 are the surfaces in front and face outward and toward each other. The midline surfaces 106 lie between the distal surfaces 102 and the mesial surfaces 104. It will be understood that the probing depth 108 will extend between the gum portion 110 and the bone 112, as determined by the practitioner.

FIG. 2B is a representative top perspective view of a common tooth showing the different surfaces of the tooth to be examined in the preferred method of the present invention. The upper surface 120 has a lingual side 122, i.e. the side on the inside of the mouth closest the tongue, and a buccal side 124, i.e. the side on the outside of the mouth. On each of the lingual sides and on each of the buccal sides of each tooth there are the three surfaces, i.e. distal, midline and mesial. It will be understood that each tooth 100, therefore, can be said to be comprised of 6 surfaces, i.e. the distal buccal surface, the midline buccal surface, the mesial buccal surface, the mesial lingual surface, the midline lingual surface and the distal lingual surface. The depth of probing will be conducted at these surfaces in a preferred embodiment of the method of the present invention.

FIG. 3 is a representative perspective view of the method and apparatus of the present invention. The periodontal examination apparatus 130, shown mounted on the examiner's forearm includes on a front side a keypad 132 that allows a user to select the desired functions and data input or recall while performing the examination. The keypad will generally include at least buttons to enter a patient's name or other identifying information, select a recording or viewing operation, select a particular tooth, select a preset program sequence, and select manual input. An LCD 134 allows the user to monitor the input and view any recalled data. The apparatus is retained by attachment means 150, also shown in FIG. 6. It is envisioned that during use, a sterilized transparent cover that can be replaced for each patient will be placed over the periodontal examination apparatus 130 in order to provide infection control. As the examiner goes through a procedure, he or she can probe and enter data without setting the probe down or moving positions.

Figure 4:
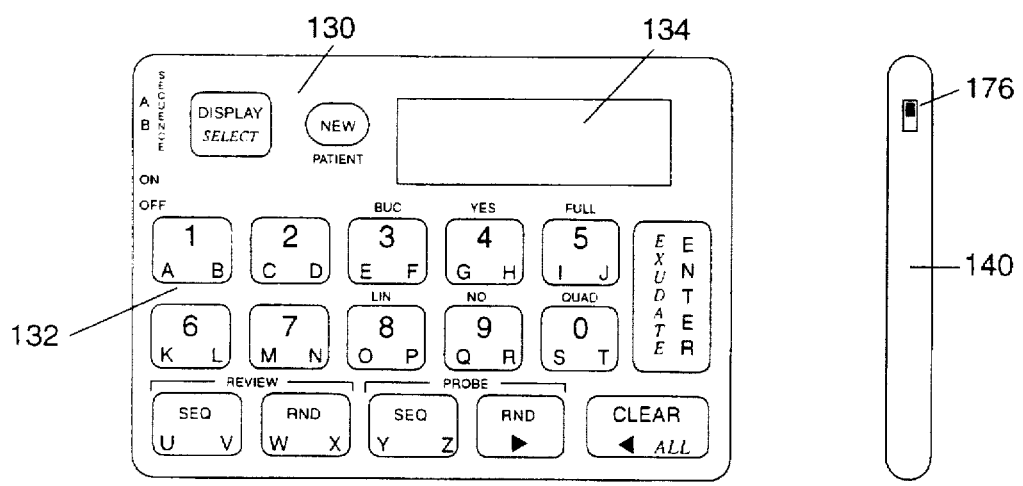
FIG. 4 is a representative top view of the keypad and display of the periodontal examination apparatus of the present invention.

FIG. 4 is a representative top view of the keypad and display of the periodontal examination apparatus of the present invention. The keypad 132 consists of a number of finger tip or touch activated buttons. A variety of types of keypads are known and will be apparent to those skilled in the art. The LCD 134 can be modified to be any type of display, including LED, flat or thin screen, colored or black and white, etc.

Figure 5:
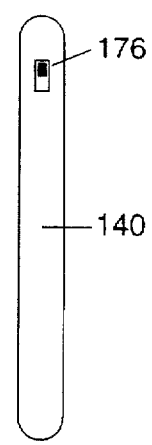
FIG. 5 is a representative side view of the method and apparatus of the present invention.

FIG. 5 is a representative side view of the method and apparatus of the present invention. It will be understood that the preferred embodiment is a thin electronic assembly which is lightweight and portable. The side portion 140 has a narrow profile.

FIG. 6 is a representative cross section view taken at section line 6 in FIG. 3 of the method and apparatus of the present invention. The attachment means 150 of the periodontal examination apparatus 130 includes an arm strap 152 which secures the apparatus to the user's arm. The arm strap 152 can be a cuff, clip, velcro strap or any other preferred attachment means for securing the apparatus securely to the user's arm or wrist. In the preferred embodiment, the mounting and securing means are a hook-and-eye type fastener such as VELCRO. This allows the user to quickly and easily take the periodontal examination apparatus on and off as many times during the day as the user wishes. It will be understood that the attachment means also includes clips, brackets, or other for securing the apparatus of the present invention to other items within the practitioner's armamentarium, such as the dental examination chair, mirrors, lamps, counters, or elsewhere.

FIG. 7 is a representative view of the periodontal examination apparatus of the present invention installed in a desktop retainer. The periodontal examination apparatus 130 can be placed in a desktop retainer 160 which will serve as a type of docking station. The periodontal examination apparatus 130 can then be linked to an additional plurality of auxiliary devices such as a label printer 162, television or computer monitor, other display means, other computer, memory or controller device, other printing devices, etc. This makes the periodontal examination apparatus 130 of the present invention very adaptable to different practitioner's personal modes of operation. The retainer 160 also serves as a battery charger for when the examiner has the apparatus on his or her wrist or for when the apparatus is otherwise positioned within the practitioner's armamentarium.

Figure 8:
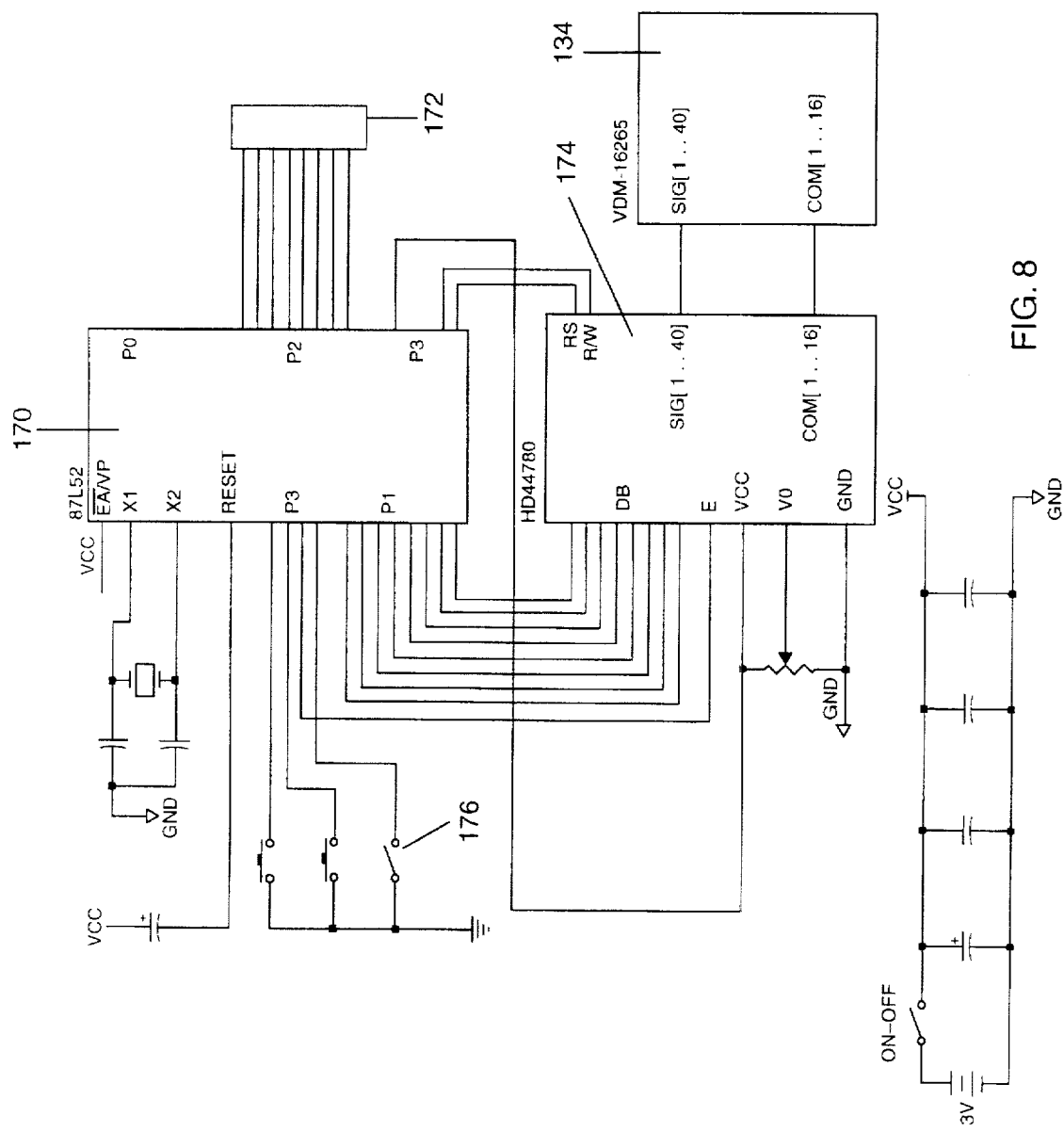
FIG. 8 is a circuit diagram for a preferred embodiment of the periodontal examination apparatus.

FIG. 8 is a circuit diagram for a preferred embodiment of the periodontal examination apparatus 130. An embodiment of the device is battery powered and is deactivated if it is left on for a given length of time with no use. A chief component of the periodontal examination apparatus 130 is a microcontroller programmable memory main controller 170. The main controller 170 receives signals from the keypad 132 through a keypad connector 172. The main controller 170 is pre-programmed to execute at least two automatic sequences when triggered. These sequences will be described in detail below. User prompts and recalled data are transmitted from the preprogrammed main controller chip 170 to the user via an LCD interface controller 174, which displays the data on the LCD 134. In a preferred embodiment, the display consists of 2 full lines each with 16 alphanumeric characters. It is recognized that other or additional interface controllers can be easily substituted to allow more lines of character display.

In a preferred embodiment, the choice between automatic sequences A and B is controlled by switch 176, which is accessed on the side of the periodontal examination apparatus 130. When the periodontal examination apparatus 130 is powered up, it will select one of the two full mouth automatic sequences, depending on the setting of switch 176. This default mode is used because one of the automatic sequences will usually be employed when the practitioner or other user is performing a full mouth examination.

Figure 9:
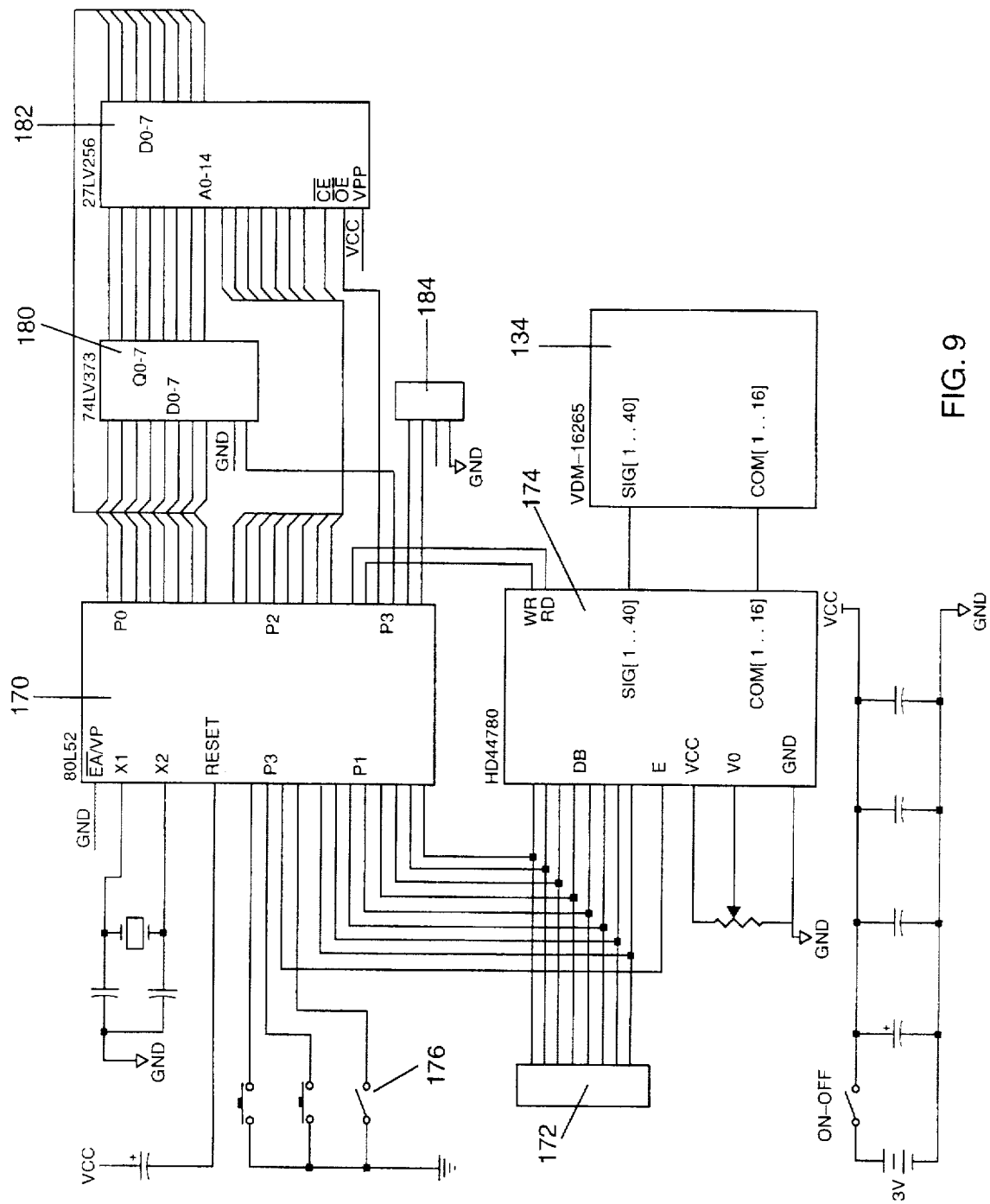
FIG. 9 is a circuit diagram for a preferred embodiment of the periodontal examination apparatus.

FIG. 9 is a circuit diagram for a preferred embodiment of the periodontal examination apparatus 130. An alternate means of constructing the controlling circuitry for the periodontal examination apparatus 130 is shown in FIG. 9. This circuit functions essentially the same as that described above, but further includes expanded internal memory 182 and its interface controller 180, utilized for such purposes as, but not limited to, additional control logic storage, software, enhanced data storage, or instructions for interconnection with an external device. Also shown in the circuit diagram is an output circuit and port 184, such as a serial or other communication port, for transmitting data from the periodontal examination apparatus 130 to an external device. As will be understood, the type of connector can be selected and adapters are available for utilizing with the present invention, their use contemplated herein and included within the scope of this invention.

Figure 10:
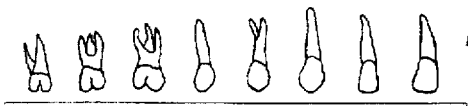
FIG. 10 is a representative form entitled "Periodontal Examination Record" for use in a preferred embodiment of the method of the present invention.

FIG. 10 is a representative form entitled "Periodontal Examination Record" for use in a preferred embodiment of the method of the present invention. This form would be similar to that provided to practitioners for use in compiling patient records and files. Each form has space allocated thereon for records from 2 complete periodontal examinations. Modifications to the form will be apparent to those skilled in the art and will be considered within the scope of this invention.

FIG. 11 is a representative printed label showing periodontal examination data collected and generated using a preferred embodiment of the method and apparatus of the present invention. As will be more apparent by the procedure described below, the label 190 will hold periodontal examination data for 8 teeth, or more or less. While it is apparent that a print-out of the periodontal examination data for all 32 teeth would be possible, a preferred embodiment of the invention utilizes labels with periodontal examination data for 8 teeth each. These labels are for use in conjunction with the forms of FIG. 10. Also shown are letters including E, M and F. These letters, as will be more fully described below, stand for exudate, mobility and furcation. At each of the six examination surfaces, the presence of bleeding or other suppuration is noted. Mobility is an important measurement which need only be recorded once per tooth. Furcation is a measurement taken only on selected surfaces of selected teeth.

Figure 12:
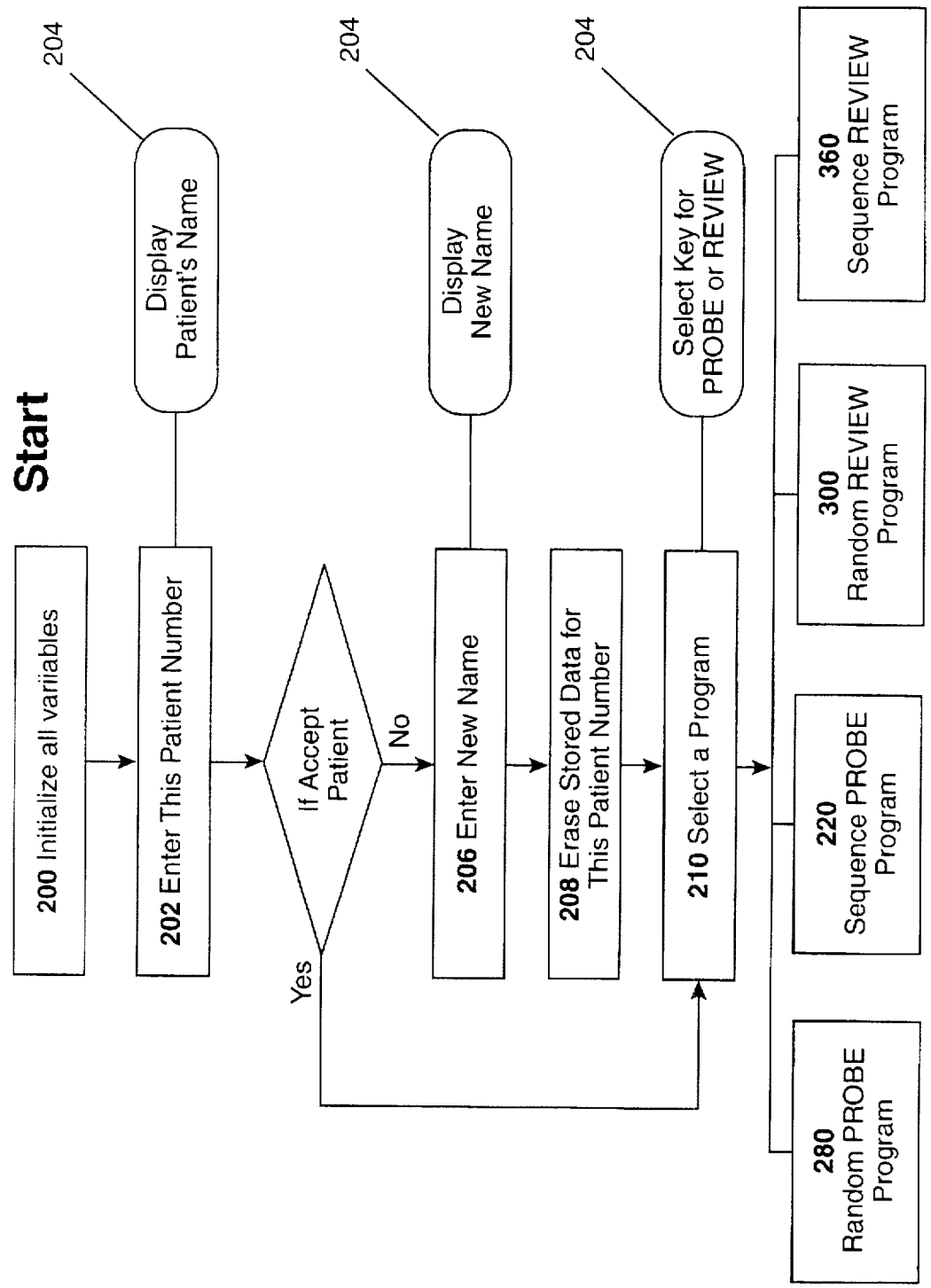
FIG. 12 is a flowchart of a preferred embodiment of the periodontal examination method of the present invention.
Figure 12:
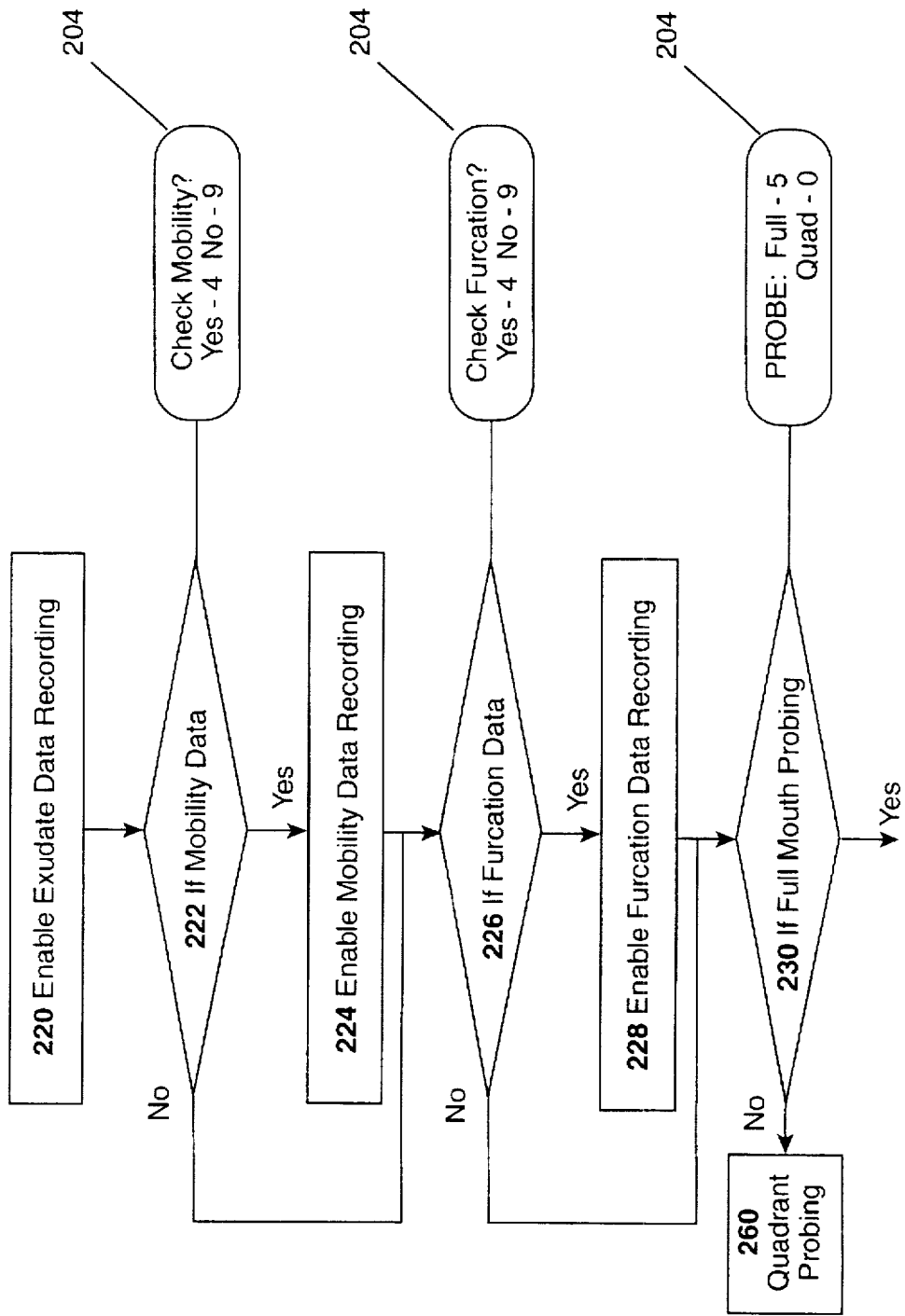
Figure 12:
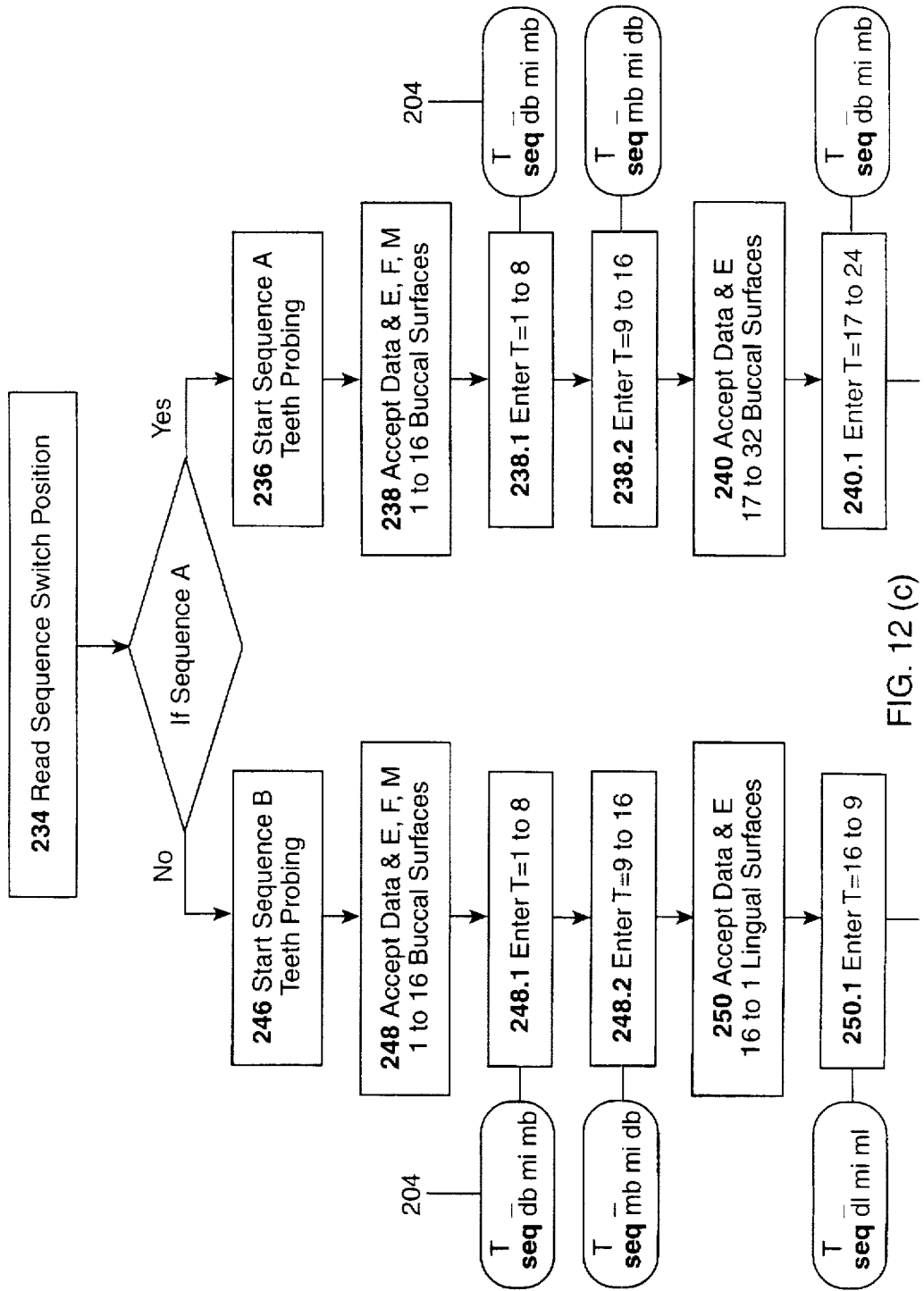
Figure 12:
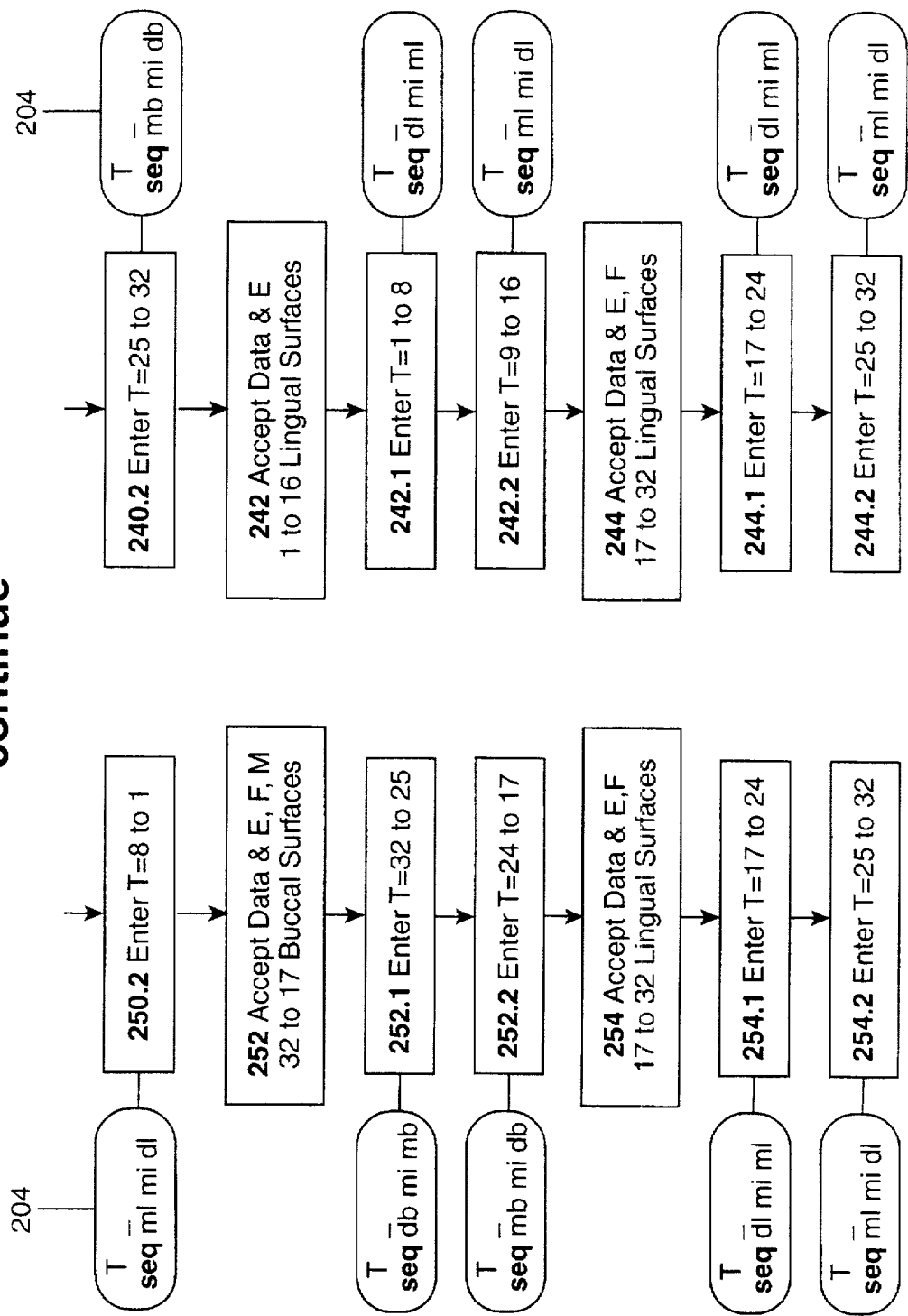
Figure 12:
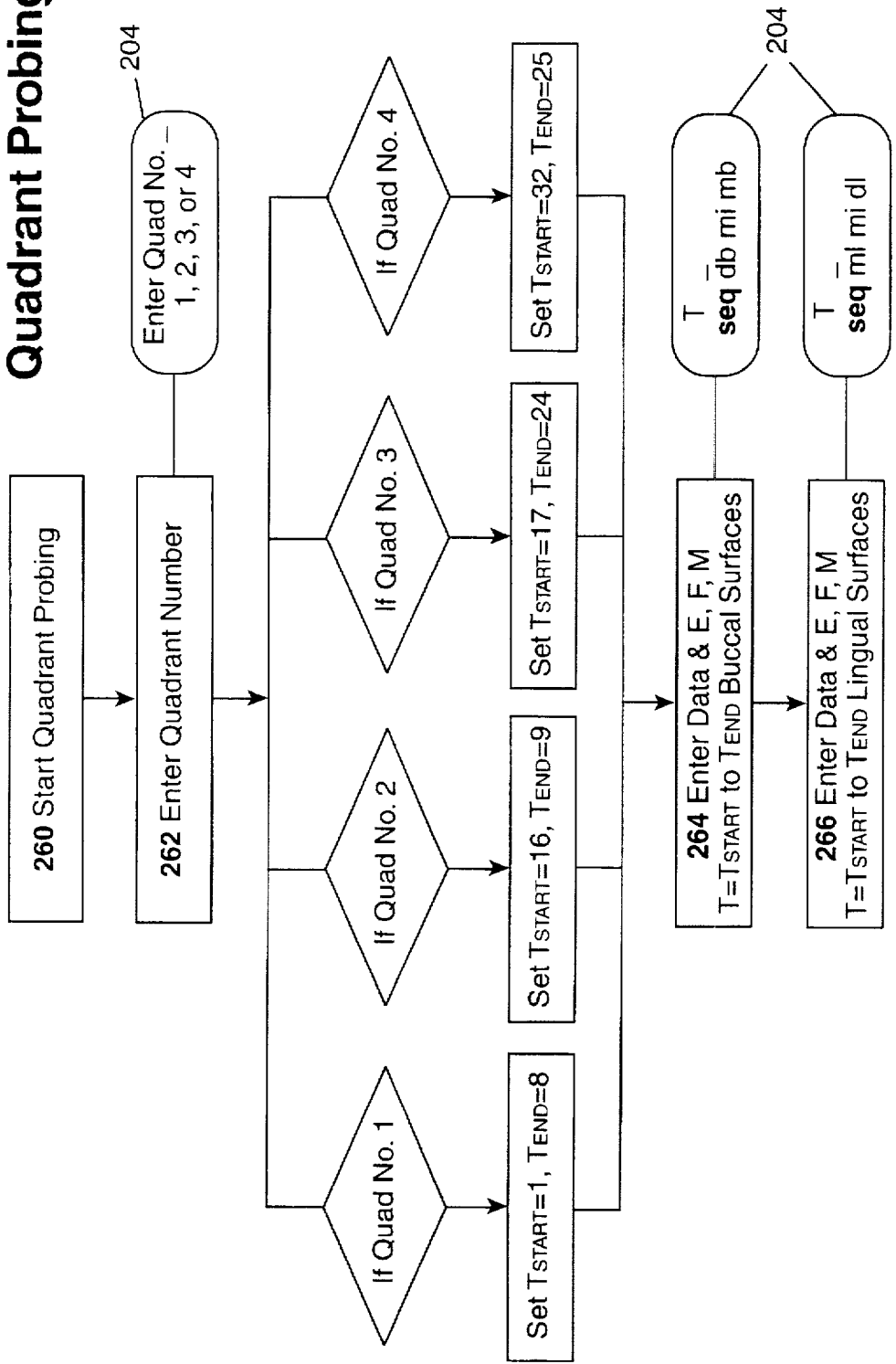
Figure 12:
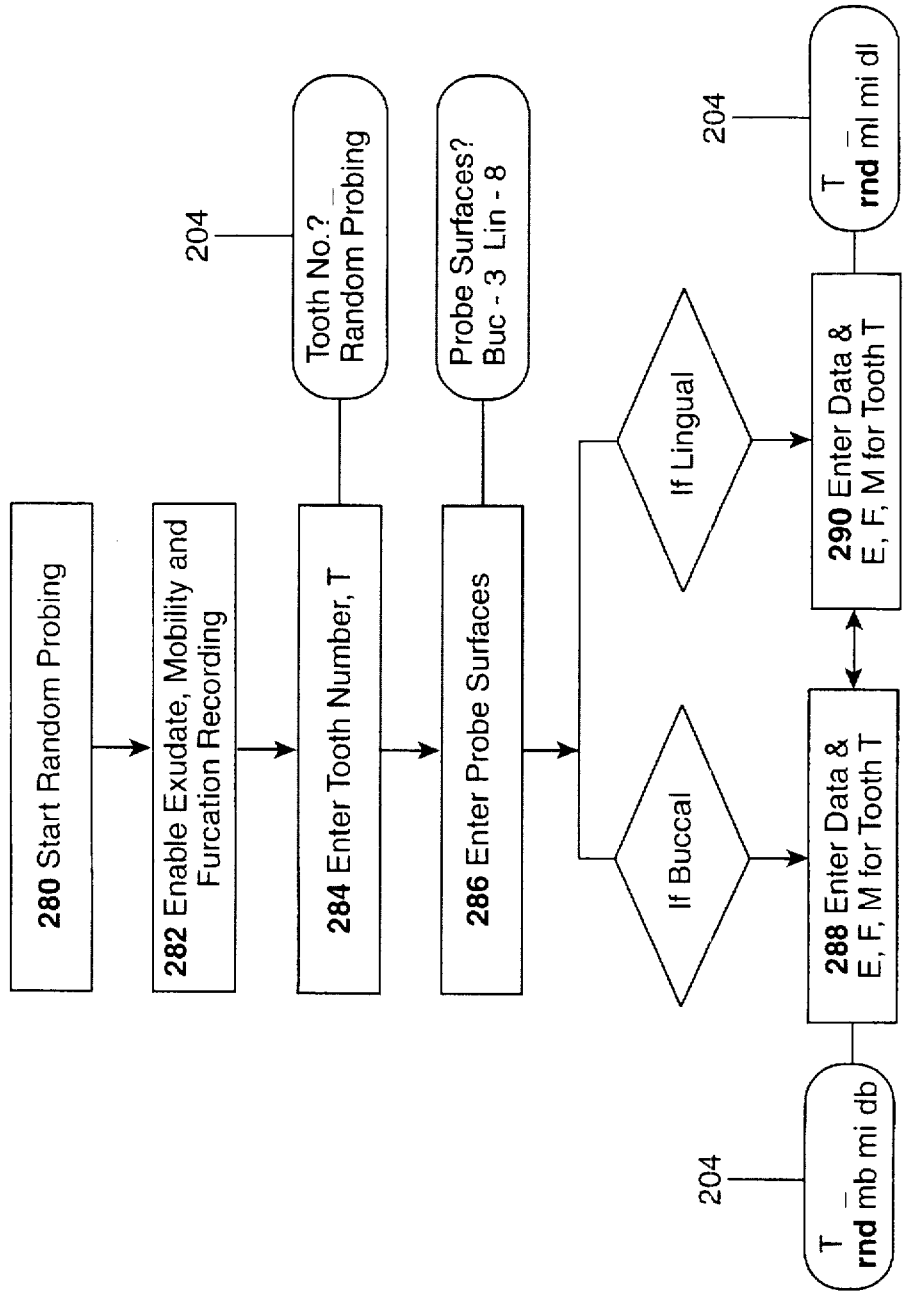
Figure 12:
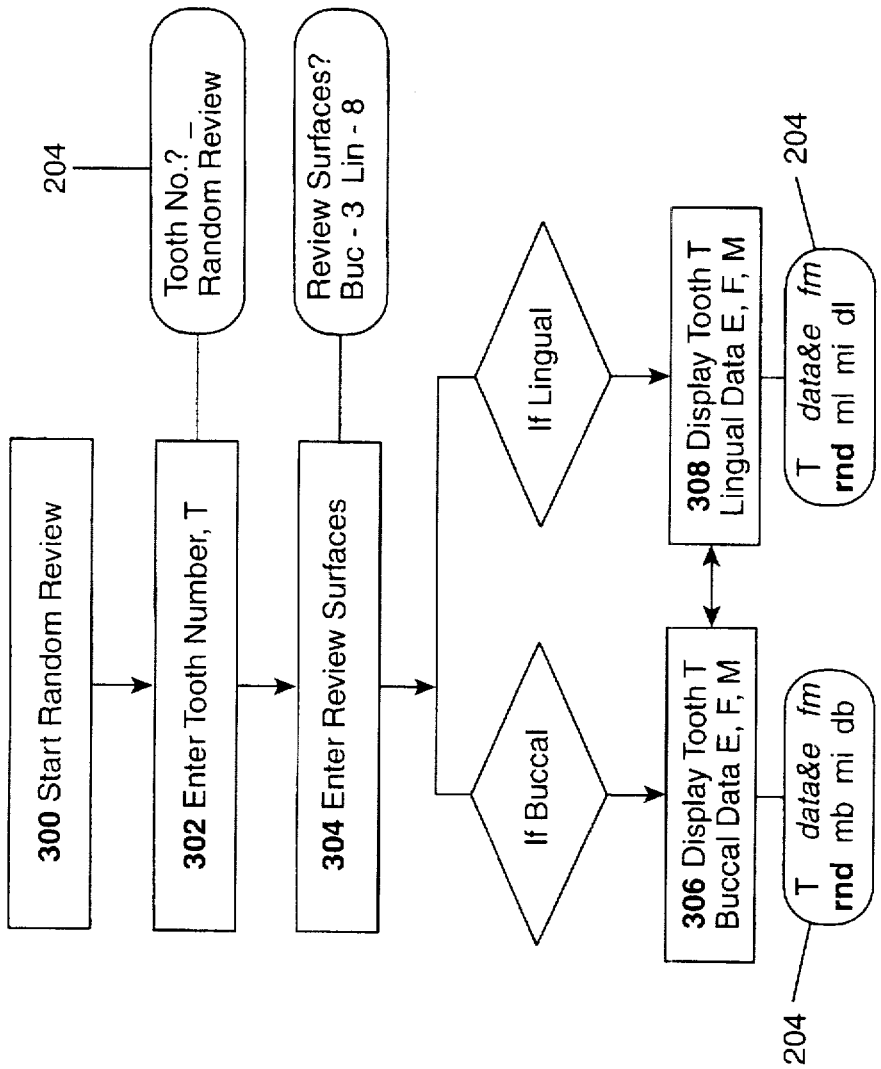
Figure 12:
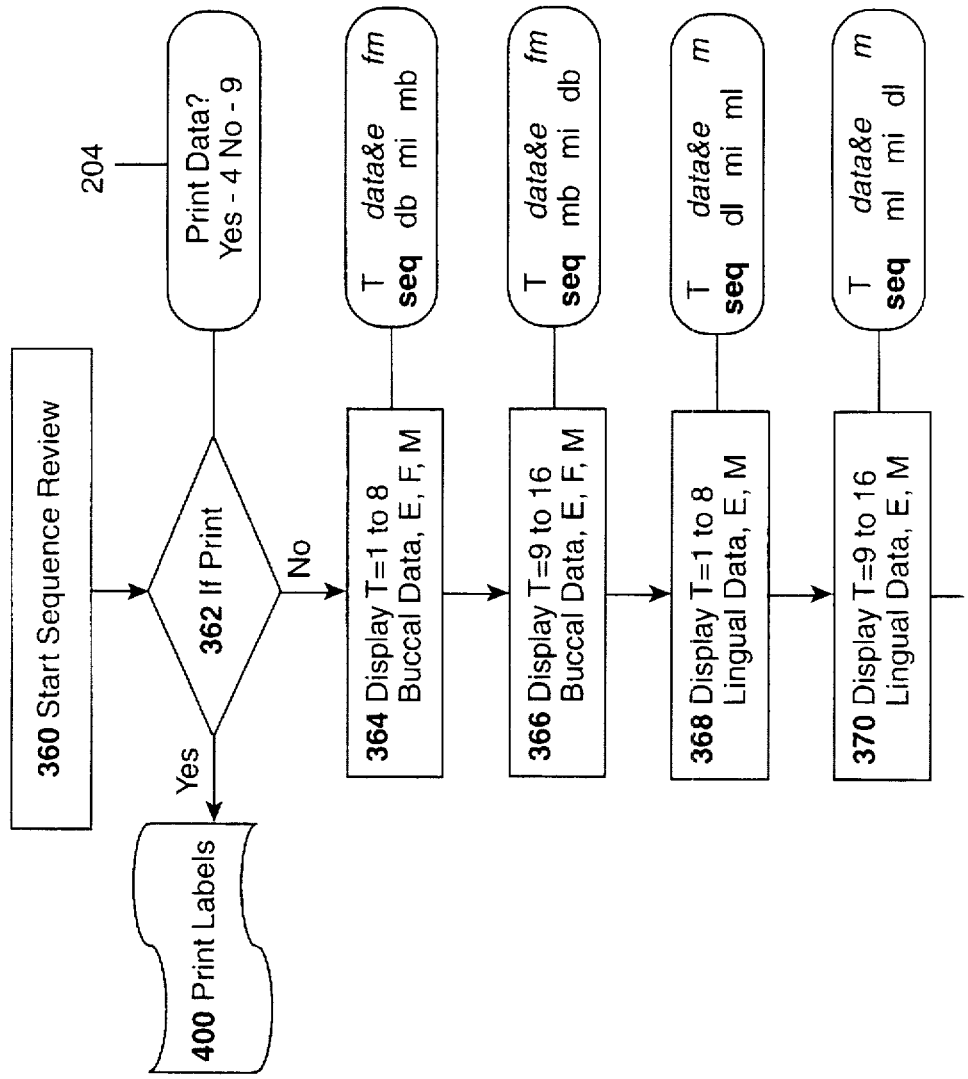
Figure 12:
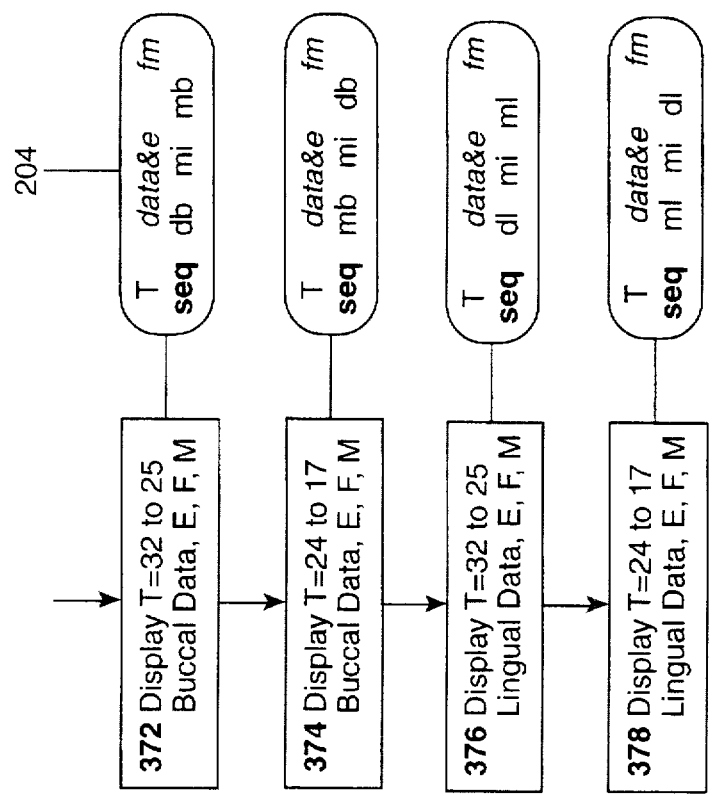

FIG. 12 is a flowchart of a preferred embodiment of the periodontal examination method of the present invention. It will be understood that the method described herein is but one of many alternate methods of use of the periodontal examination apparatus of the present invention. Such variations and modifications will be considered within the scope of the present invention. References are to the representative top view of the keypad and display of the periodontal examination apparatus 130 of the present invention.

One purpose of the periodontal examination is to examine the shape, topography and dimensions of pockets or similar defects in the patient's bone between and around the roots of the teeth and the gums. A principle tool of the periodontal examination is the periodontal probe. The probe generally consists of a handle, and angled shaft and the working end of the probe. The working end is slender and rod-like, may be straight or tapered, and has a series of marks indicating distances, usually in millimeters. Pocket depth is measured from the top of the junctional epithelium to the gingival margin, or elsewhere. By measuring the six surfaces of the tooth as disclosed above, a very accurate understanding and visualization of the topography and nature of any defects in the bone/tooth interface can be gained.

Other indicators of periodontal health can be accumulated during the periodontal examination. The presence of exudate is indicative of periodontal disease. Exudate is material composed of serum, fibrin, and white blood cells in variable amounts that escapes from blood vessels into a superficial lesion of an area of inflammation. Often exudation is accompanied by bleeding.

Because of the nature and function of the periodontal ligament, teeth have a slight normal mobility. Mobility can be considered abnormal or pathological when such mobility exceeds normal. Increased mobility can be an important clinical sign of disease.

Furcation is the area or region lying between and at the base of two or more normal anatomically divided roots. In periodontology, furcation involvement means that the pocket and bone loss have extended into the furcation area between the roots of a multirooted tooth. Thus, evidence of furcation involvement need only be investigated, and recorded if present, for certain teeth, namely the molars. In the periodontal examination, one record for the buccal side of each of teeth numbered 1, 2, 3, 5, 12, 14, 15, 16 is made. Two additional records, for the buccal and lingual sides for each of teeth 17, 18, 19, 30, 31, and 32 can also be taken.

Step 200 is an initialization step in a preferred embodiment of the operating program utilized with the present invention. Subsequent to initialization of the system, a patient identifier number or other code is entered in step 202. This is done by sequentially pressing the letters of the patient's name on the appropriate keys of the keypad. If the patient has been seen by the practitioner in the past or periodontal examination data exists in the system for the patient, the patient's name is displayed on the LCD or elsewhere in display 204. If not, the patient's name can be entered for display in step 206. Furthermore, if stored periodontal examination data exists for the patient or if the patient number had been previously assigned, such stored periodontal examination data is erased in step 208.

In either case, once a patient has been entered and accepted by the operating program, in step 210 the practitioner must select whether he or she will be reviewing stored periodontal examination data or will be probing teeth and entering new periodontal examination data. In a preferred embodiment of the method and apparatus of the present invention, the practitioner will select between a random probe program 280, a sequence probe program 220, a random review program 300 or a sequence review program 360.

If sequence probe program is selected, the first subroutine executed by the apparatus is to enable exudate data recording in step 220. Subsequently, if mobility data is desired, the practitioner will respond accordingly in step 222. If mobility data is desired, subroutine 224 to record mobility data is enabled. Subsequently, if furcation data is desired, the practitioner will respond accordingly in step 226. If furcation data is desired, subroutine 228 to record furcation is enabled.

In step 230 the practitioner is presented with the option of probing either a full mouth or one or more individual quadrants. The practitioner can proceed with probing an individual quadrant in step 260 or can proceed to select a preprogrammed sequence. In step 234, the operating program will read the position of the sequence switch 176 and proceed to initiate sequence A or B.

Using the numbering system for teeth given in FIG. 1, a first automatic sequence, initiated in step 236 of the operating program of the periodontal examination apparatus 130 accepts periodontal examination data input sequentially for the three buccal surfaces of teeth 1–32, steps 238 and 240 in order (distal, midline and mesial for each of teeth 1–8 in step 238.1 and then mesial, midline and distal for each of teeth 9–16 in step 238.2, distal, midline and mesial for each of teeth 17–24 in step 240.1 and then mesial, midline and distal for each of teeth 25–32 in step 240.2). It will be understood that in a preferred embodiment, when teeth are probed, probe data is entered in integer format, individual values ranging between 0 and 14 (typically referring to standard units of millimeters). The display will prompt the examiner as he or she performs the examination for certain information by showing a tooth number with a series of surface indicators as shown in the display 204 adjacent the given step in the flowchart. A query for mobility is made automatically once for each of the teeth. Presence of exudate can be noted for every tooth by touching the display/select key and then touching the enter/exudate key. This would be done at each surface. If furcation has been enabled, the display will automatically query the examiner at each surface where furcation is to be measured.

Proceeding through sequence A, the apparatus then accepts periodontal examination data sequentially for the three lingual surfaces of teeth 1–32, steps 242 and 244 in order (distal, midline and mesial for each of teeth 1–8 in step 242.1 and then mesial, midline and distal for each of teeth 9–16 in step 242.2, distal, midline and mesial for each of teeth 17–24 in step 244.1 and then mesial, midline and distal for each of teeth 25–32 in step 242.2). During these operations, as pointed out above, the display will not query the examiner again for mobility data and it will only query the examiner for furcation data for certain teeth, as outlined above.

A second automatic sequence, initiated in step 246, accepts periodontal examination data for the three buccal surfaces of teeth 1–16 in step 248 (distal, midline and mesial for each of teeth 1–8 in step 248.1 and then mesial, midline and distal for each of teeth 9–16 in step 248.2), then for the three remaining lingual surfaces of teeth 16–1 in step 250 (distal, midline and mesial for each of teeth 16–9 in step 250.1 and then mesial, midline and distal for each of teeth 8–1 in step 250.2). The sequence continues with recording periodontal examination data for the three buccal surfaces of teeth 32–17 in step 252, and finally, to the three remaining lingual surfaces of teeth 17–32 in step 254. Appropriate exudate data can be recorded as noted above and recordation of mobility data and furcation data will be prompted, as enabled and preprogrammed.

Alternatively, the examiner in step 210 can select to start probing individual quadrants. Such examination can be initiated in step 260, and the quadrant number can be input to the system in step 262. If, for example, quadrant no. 1 is selected, teeth are assigned values of first through eighth, these values corresponding to different teeth for different quadrants. Thus, teeth are probed in the order of first through eighth. Distal buccal surface, midline buccal surface and mesial buccal surface periodontal examination data is entered into the system by the practitioner in step 264. Lingual surfaces are probed in the reverse order from 8 to 1, from mesial to midline to distal, the information entered in step 266. If the examiner chooses to examine only a quadrant, the appropriate probe sequence will be selected on the keypad 132. As before, E, M and F data can also be recorded and will be prompted when appropriate.

If, however, the examiner selects a random mode of operation in step 280, the apparatus will enable exudate, mobility and furcation in step 282 and the examiner will enter the desired tooth number in step 284 as prompted by display 204. A choice of probing either the buccal or the lingual surfaces is presented and the examiner enters the desired side in step 286. Thus, if buccal side surfaces are selected, periodontal examination data corresponding to the mesial buccal surface, the midline buccal surface and the distal buccal surface can be entered, along with E, F or M data, as prompted in step 288. Alternatively, if or when lingual if buccal side surfaces are selected, periodontal examination data corresponding to the mesial lingual surface, the midline lingual surface and the distal lingual surface can be entered, along with E, F or M data, as prompted in step 290.

If the examiner selects, in step 210 random review program 300, the tooth number of any random tooth can be entered in step 302 at a prompt. This time, the examiner will select to review either buccal or lingual periodontal examination data in step 304. Thus, periodontal examination data for the buccal surfaces will be displayed in step 306, or, periodontal examination data for the lingual surfaces will be displayed in step 308. Appropriate displays will show the periodontal examination data for the surfaces including E, M and F data, where and when present.

Alternatively, the examiner may select to review periodontal examination data for teeth sequentially in step 210. Once initiated, sequence review program 360 will prompt the examiner or other operator for printing instructions entered in step 362. Periodontal examination data can either be printed in step 400 or reviewed, first quadrant buccal side surfaces in step 364, second quadrant buccal side surfaces in step 366, first quadrant lingual side surfaces in step 368, second quadrant lingual surfaces in step 370, fourth quadrant buccal side surfaces in step 372, third quadrant buccal side surfaces in step 374, fourth quadrant lingual side surfaces in step 376, or third quadrant lingual surfaces in step 378, all displays including E, M and F data, where and when present.

It will be understood by the foregoing that anytime certain keys are selected on the keypad, the operating mode can be interrupted and the examiner is free to continue with a certain examination or review sequence or random examination or review. Furthermore, an embodiment of the apparatus comprises an enhanced set of operating parameters, instructions, sequences and options for the examiner. Furthermore, the examiner will have the ability to program the device to accept other type of data, as the examiner may desire, and to customize the sequencing, display and keystrokes required for his or her preferred technique or record keeping requirements.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A periodontal examination apparatus for recording and recall of periodontal examination data by an examiner, the apparatus comprising:

a main controller with an operating program for recording of periodontal examination data and recall of periodontal examination data functions;

keypad entry means to activate input for recording of periodontal examination data, and to activate recall of periodontal examination data functions;

display means to display user prompts and recalled periodontal examination data;

memory means for periodontal examination data and program storage, wherein said main controller's operating program stores periodontal examination data for future use, including review and display, in the memory means, the memory means accepting periodontal examination data in at least one predetermined examination sequence, the memory means also accepting periodontal examination data in a random sequence; and attachment means for securing the periodontal examination apparatus in an operable position for use by the examiner.

2. The periodontal examination apparatus of claim 1 further comprising:

interface means to transmit periodontal examination data from the memory means to an external device.

3. The periodontal examination apparatus of claim 2 in which the interface means transmits periodontal examination data to a label printer.

4. The periodontal examination apparatus of claim 1 in which the operating program allows the memory means to accept periodontal examination data in a plurality of predetermined examination sequences, the apparatus further comprising:

switch means to enable the examiner to activate at least one of the plurality of predetermined examination sequences.

5. The periodontal examination apparatus of claim 1 wherein the number of predetermined examination sequences is two for full mouth examinations, and four for individual quadrant sequences.

6. The periodontal examination apparatus of claim 1 in which the attachment means is an arm strap.

7. The periodontal examination apparatus of claim 1 in which the attachment means is a clamp.

* * * * *